US 8,329,471 B2

(12) United States Patent
Jin et al.

(10) Patent No.: US 8,329,471 B2
(45) Date of Patent: *Dec. 11, 2012

(54) ISOLATED POPULATION OF PLANT SINGLE CELLS AND METHOD OF PREPARING SAME

(75) Inventors: Young Woo Jin, Jeonju (KR); Eun Kyong Lee, Iksan (KR)

(73) Assignee: Unhwa Corporation (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/889,126

(22) Filed: Sep. 23, 2010

(65) Prior Publication Data

US 2011/0039312 A1 Feb. 17, 2011

Related U.S. Application Data

(63) Continuation of application No. 12/117,783, filed on May 9, 2008, now Pat. No. 8,053,238, which is a continuation-in-part of application No. 12/063,929, filed as application No. PCT/KR2006/001544 on Apr. 25, 2006, now Pat. No. 8,017,397.

(30) Foreign Application Priority Data

Oct. 31, 2005 (KR) ........................ 10-2005-0103445

(51) Int. Cl.
C12N 5/00 (2006.01)
C12N 5/02 (2006.01)
(52) U.S. Cl. ........................................ 435/422; 435/410
(58) Field of Classification Search .................. 435/422, 435/410
See application file for complete search history.

(56) References Cited

U.S. PATENT DOCUMENTS

| 5,019,504 A | 5/1991 | Christen et al. |
| 5,344,775 A | 9/1994 | Smith |
| 5,407,816 A * | 4/1995 | Bringi et al. ................... 435/123 |
| 5,550,318 A * | 8/1996 | Adams et al. ................ 800/300.1 |
| 8,017,397 B2 | 9/2011 | Jin et al. |
| 8,053,238 B2 | 11/2011 | Jin et al. |
| 2008/0194025 A1 | 8/2008 | Jin |
| 2009/0011477 A1 | 1/2009 | Jin |
| 2010/0233813 A1 | 9/2010 | Jang et al. |
| 2010/0255585 A1 | 10/2010 | Yu et al. |
| 2010/0272692 A1 | 10/2010 | Park et al. |

(Continued)

FOREIGN PATENT DOCUMENTS

EP 1538214 A1 6/2005

(Continued)

OTHER PUBLICATIONS

Ziv, M; "Bioreactor Technology for Plant Micropropagation," Horticultural Reviews, vol. 24, 2000, pp. 1-30.*

(Continued)

*Primary Examiner* — Susan McCormick Ewoldt
(74) *Attorney, Agent, or Firm* — Sterne, Kessler, Goldstein & Fox P.L.L.C.

(57) ABSTRACT

This invention is a method of minimizing the variation of cell growth and production through homogeneous cell line development. To be more specific, it is the method of isolating and proliferating single cell clone from cambium or procambium to promote the stability of the plant-derived biologically active substances production by solving the problems of decrease in cell growth and the productivity during the long term culture.

31 Claims, 5 Drawing Sheets

U.S. PATENT DOCUMENTS

| | | |
|---|---|---|
| 2011/0033903 A1 | 2/2011 | Jin |
| 2011/0039312 A1 | 2/2011 | Jin |
| 2011/0097310 A1 | 4/2011 | Jang et al. |
| 2011/0117039 A1 | 5/2011 | Lee et al. |
| 2011/0217273 A1 | 9/2011 | Hong et al. |
| 2011/0229443 A1 | 9/2011 | Jin et al. |

FOREIGN PATENT DOCUMENTS

| | | |
|---|---|---|
| EP | 2399596 A1 | 12/2011 |
| KR | 1997-0009157 B1 | 6/1997 |
| KR | 10-2000-0056501 A | 9/2000 |
| KR | 10-0290004 B1 | 5/2001 |
| KR | 2001-0094111 A | 10/2001 |
| KR | 10-2004-0108052 A | 7/2003 |
| KR | 2003-0063724 A | 7/2003 |
| KR | 10-2004-0014584 A | 2/2004 |
| KR | 2004-0108052 | 12/2004 |
| KR | 10-2005-0041259 A | 5/2005 |
| KR | 10-2005-0078372 A | 8/2005 |
| KR | 10-2005-0102571 A | 10/2005 |
| WO | WO 93/17121 A1 | 9/1993 |
| WO | WO 2007/052876 A1 | 5/2007 |
| WO | WO 2009/048306 A1 | 4/2009 |
| WO | WO 2009/139581 A2 | 11/2009 |
| WO | WO 2009/151302 A2 | 12/2009 |
| WO | WO 2010/019016 A2 | 2/2010 |
| WO | WO 2010/038991 A2 | 4/2010 |
| WO | WO 2010/095911 A2 | 8/2010 |

OTHER PUBLICATIONS

Naill et al. "Preparation of Single Cells From Aggregated Taxus Suspension Cultures for Population Analysis," Biotechnology and Bioengineering , vol. 86, No. 7, Jun. 30, 2004, pp. 817-826.*

Roberts et al. "A simple method for enhancing paclitaxel release from Taxus Canadensis cell suspension culture utilizing cell wall digesting enzymes," Plant Cell Rep (2003) 21:1217-1220.*

European Search Report from Application No. 06 757 522.5, Aug. 2010.

Baebler, S., et al., "Establishment of cell suspension cultures of Yew (*Taxus x Media* Rehd.) and assessment of their genomic stability," *In Vitro Cell. Dev. Biol. Plant* 41:338-43, Society for In Vitro Biology, United States (May-Jun. 2005).

Bai, J., et al., "Production of biologically active taxoids by a callus culture of *Taxus cuspidata*," *J. Nat. Prod.* 67(1):58-63, American Society of Pharmacognosy, United States (Jan. 2004).

Ben Jouira, H., et al., "Adventitious shoot production from strips of stem in the Dutch elm hybrid 'Commelin': plantlet regeneration and neomycin sensitivity," *Plant Cell Tissue and Organ Culture* 53(2):153-60, Klewer Academic Publishers, Netherlands (1998).

Dodds, J.H., and Roberts, L.W., *Experiments in Plant Tissue Culture*, Third Edition, pp. 92-95, Cambridge University Press, England (1999).

Esau, K., *Anatomy of Seed Plants*, Second Edition, pp. 30, John Wiley & Sons, Inc., United States (1977).

Frankenstein, C., et al., "The onset of cambium activity—a matter of agreement?," *Dendrochronologia* (23):57-62, Elsevier GmbH, Italy (2005).

Freeman, S., *Biological Science*, Second Edition, pp. 823, Pearson Education, Inc., United States (2005).

Gibson, D.M., et al., "Initiation and growth of cell lines of *Taxus brevifolia* (Pacific yew)," *Plant Cell Reports* 12(9):479-482, Springer-Verlag, United States (1993).

Hirasuna, T.J., et al., "Taxol production in suspension cultures of *Taxus baccata*," *Plant Cell Tissue and Organ Culture* 44(2):95-102, Klewer Academic Publishers, Netherlands (1996).

Kim, M.H., et al., "Growth promotion of *Taxus brevifolia* cell suspension culture using conditional medium," *Biotechnol. Bioprocess Eng.* 5:350-4, Korean Society for Biotechnology and Bioengineering, Korea (2000).

Kumar, A., et al. "Morphogenetic responses of cultured cells of cambial origin of a mature tree—*Dalbergia sissoo* Roxb," *Plant Cell Rep.* 9(12):703-706, Springer-Verlag, Germany (1991).

Lee, E-K., et al., "Cultured cambial meristematic cells as a source of plant natural products," *Nat. Biotechnol.* 28(11):1213-7, Nature America Publishing, United States (Nov. 2010; Epub Oct. 24, 2010).

Naill, M.C., et al., "Preparation of Single Cells From Aggregated Taxus Suspension Cultures for Population Analysis," *Biotechnol. and Bioeng.* 86(7):817-26, Wiley, United States (2004).

Naill, M.C., et al., "Culture of isolated single cells from Taxus suspensions for the propagation of superior cell populations," *Biotechnol. Lett.* 27(21):1725-30, Kluwer Academic Publishers, Netherlands (2005).

Naill, M.C., et al., "Flow Cytometric Identification of Paclitaxel-Accumulating Subpopulations," *Biotechnol. Prog.* 21(3):978-83, American Institute of Chemical Engingeers, United States (2005).

Pyo, S-H., et al. "Efficient purification and morphology characterization of paclitaxel from cell cultures of *Taxus chinensis*," *J. Chem. Technol. Biotechnol.* 79(10):1162-8, Society of Chemical Industry, England (Oct. 2004, Epub Sep. 3, 2004).

Reynolds, L.B., "Effects of harvest date on some chemical and physical characteristics of American Ginseng (*Panax quinquefolius* L.)," *J. Herbs Spices and Medicinal Plants* 6(2):63-69, The Haworth Press Inc., United States (1998).

Roberts, S., and Kolewe, M., "Plant natural products from cultured multipotent cells," *Nature Biotechnol.* 28(11):1175-6, Nature America Publishing, United States (Nov. 2010).

Roberts, S.C., et al. "A simple method for enhancing paclitaxel release from *Taxus canadensis* cell suspension cultures utilizing cell wall digesting enzymes," *Plant Cell Rep.* 21(12):1217-20, Springer, Germany (Aug. 2003; Epub Jun. 17, 2003).

Strobel, G.A., et al., "Taxol formation in yew—*Taxus*," *Plant Sci.* 92:1-12, Elsevier Scientific Publishers Ireland Ltd., Ireland (1993).

Wang, C., et al., "Enhanced taxol production and release in *Taxus chinensis* cell suspension cultures with selected organic solvents and sucrose feeding," *Biotechnol. Prog.* 17(1):89-94, American Institute of Chemical Engineers, United States (Jan.-Feb. 2001).

Wang, C., et al., "Enhancement of Taxol production and excertion in *Taxus chinensis* cell culture by fungal elicitation and medium renewal," *Appl. Microbiol. Biotechnol.* 55(4):404-10, Springer International, Germany (May 2001).

White, P.R., "Potentially unlimited growth of excised plant callus in an artificial nutrient," *American Journal of Botany* 26(2):59-64, Botanical Society of America, United States (1939).

Wickremesinhe, E.R.M., and Arteca, R.N., "*Taxus* cell suspension cultures: optimizing growth and production of taxol," *J. Plant Physiol.* 144:183-8, Urban & Fischer Verlag, Germany (1994).

Wu, J., and Lin, L., "Enhancement of taxol production and release in *Taxus chinensis* cell cultures by ultrasound, methyl jasmonate and in situ solvent extraction," *Appl. Microbiol. Biotechnol.* 62(2-3):151-5, Springer Verlag, Germany (Aug. 2003; Epub Mar. 13, 2003).

Ye, Z-H., "Vascular tissue differentiation and pattern formation in plants," *Annu. Rev. Plant Biol.* 53:183-202, Annual Reviews Inc., United States (2002).

Yokoi, H., et al., "High density cultivation of plant cells in a new aeration-agitation type fermentor," *Journal of Fermentation and Bioengineering* 75(1):48-52, Society for Biotechnology, Japan (1993).

Yukimune, Y., et al., "Methyl jasmonate-induced overproduction of paclitaxel and baccatin III in *Taxus* cell suspension cultures," *Nat. Biotechnol.* 14(9):1129-32, Nature America Publishing, United States (Sep. 1996).

Zhang, C.H., et al., "Enhanced paclitaxel production induced by the combination of elicitors in cell suspension cultures of *Taxus chinensis*," *Biotechnol. Lett.* 22:1561-4, Kluwer Academic Publishers, Netherlands (2000).

Zhong, J., "Plant Cell Culture for Production of Paclitaxel and Other Taxanes," *J. Biosci. Bioeng.* 94(6):591-9, Society for Bioscience and Bioengineering, Japan (2002).

Ziv, M., "Bioreactor technology for plant micropropagation," *Hortic. Rev.* 24:1-30, AVI Pub. Co., United States (2000).

Office Action in Australian Appl. No. 2008202078, inventor Jin, Y.W., with a filing date of May 9, 2008, mailed Aug. 17, 2010, issued by Australian Patent Office, Australia.

English language Abstract of Korean Patent Publication No. KR1997-0009157 B1, European Patent Office, espacenet database—Worldwide, (1997).
English language Abstract of Korean Patent Publication No. KR 2001-0094111 A, European Patent Office, espacenet database—Worldwide, (2001).
English language Abstract of Korean Patent Publication No. KR10-0290004 B1, European Patent Office, espacenet database—Worldwide, (2001).
English language Abstract of WIPO Patent Publication No. WO 2009/139581 A2, European Patent Office, espacenet database—Worldwide, (2009).
English language Abstract of WIPO Patent Publication No. WO 2009/151302 A2, European Patent Office, espacenet database—Worldwide, (2009).
English language Abstract of WIPO Patent Publication No. WO 2010/019016 A2, European Patent Office, espacenet database—Worldwide, (2010).
English language Abstract of WIPO Patent Publication No. WO 2010/038991 A2, European Patent Office, espacenet database—Worldwide, (2010).
English language Abstract of WIPO Patent Publication No. WO 2010/095911 A2, European Patent Office, espacenet database—Worldwide, (2010).
English language Abstract of Korean Patent Publication No. KR 2003-0063724 A, European Patent Office, espacenet database—Worldwide, (2001).
English language Abstract of Korean Patent Publication No. KR 2004-0108052 A, European Patent Office, espacenet database—Worldwide, (2001).
International Search Report with Written Opinion of the International Searching Authority for International Application No. PCT/KR2006/001544, mailed on Jun. 28, 2006, Korean Intellectual Property Office, Korea.
Reply to Office Action in U.S. Appl. No. 12/063,929, inventor Jin, Y.W., et al., with a 371(c) date of Apr. 25, 2006, filed Dec. 16, 2010, U.S. Patent and Trademark Office, Alexandria, VA.
Election/Restriction Requirement in U.S. Appl. No. 12/063,929, inventors Jin, Y.W., et al., with a 371(c) date of Apr. 25, 2006 mailed, Aug. 31, 2009, U.S. Patent and Trademark Office, Alexandria, VA.
Office Action in U.S. Appl. No. 12/063,929, inventors Jin, Y.W., et al., with a 371(c) date of Apr. 25, 2006, electronic notification date of May 13, 2010, U.S. Patent and Trademark Office, Alexandria, VA.
Office Action in U.S. Appl. No. 12/063,929, inventors Jin, Y.W., et al., with a 371(c) date of Apr. 25, 2006, electronic notification date of May 16, 2010, U.S. Patent and Trademark Office, Alexandria, VA.
Office Action in U.S. Appl. No. 12/117,783, inventors Jin, Y.W., et al., with a 371(c) date of May 9, 2008, mailed Mar. 5, 2009, U.S. Patent and Trademark Office, Alexandria, VA.
Office Action in U.S. Appl. No. 12/117,783, inventors Jin, Y.W., et al., with a 371(c) date of May 9, 2008, mailed Jun. 16, 2010, U.S. Patent and Trademark Office, Alexandria, VA.
Office Action in U.S. Appl. No. 12/117,783, inventors Jin, Y.W., et al., with a 371(c) date of May 9, 2008, mailed Sep. 17, 2009, U.S. Patent and Trademark Office, Alexandria, VA.
Co-pending Application, U.S. Appl. No. 13/058,949, inventors Jin, et al., filed Aug. 14, 2009 (Not Yet Published).
Australian Patent Office Search Report for Application No. SG 201001806-7, mailed Jul. 20, 2010.
Australian Patent Office Written Opinion for Application No. SG 201001806-7, mailed Jul. 20, 2010.

Teng, W.L., et al., "Explant preparation affects culture initiation and regeneration of Panax ginseng and Panax quinquefolius," *Plant Cell* 68:233-239, Springer-Verlag, United States (2002).
Verdeil, JL, et al., "Pluripotent versus totipotent plant stem cells: dependence versus autonomy," *Trends Plant Sci.* 12(6):245-52, Elsevier Science, England (2007)
Supplementary European Search Report for European Patent Application No. EP08832692, which is counterpart to PCT/KR2008005605, dated Dec. 2, 2010.
Antoni, H.J. and Folquer, F.,"Cultivo "In Vitro" de Tejidos de Batatas *Ipomoea batatas* (L.) Lam. Para La Produccion de Nuevos Cultivares," *Revisita Agronomica del Noroeste Argentino* 12(1-2):177-8, Universidad Nacional de Tucuman, Facultad de Agronomia y Zootecnia, Argentina (1975) (Spanish Language).
Asaka, I., et al., "Embryoid Formation by High Temperature Treatment from Multiple Shoots of *Panax ginseng,*" *Planta Med.* 59(4):345-6, George Thieme, United States (Aug. 1993).
Kitin, P., et al., "Analysis by Confocal Microscopy of the Structure of Cambium in the Hardwood *Kalopanax pictus*," Annals of Botany 86: 1109-1117, Annals of Botany Company, United States (2000).
Lachaud, S., et al., "Structure and functions of the vascular cambium," *C. R. Acad. Sci. III.* 322(8):633-50, Elsevier, France (Aug. 1999).
West, G., et al., "Cell Cycle Modulation in the Response of thePrimary Root of Arabidopsis to Salt Stress," *Plant Physiology* 135:1050-1058, American Society of Plant Biologists, United States (Jun. 2004).
Woodward, A.W., and Bartel, B., "Auxin: Regulation, Action, and Interaction," Annals of Botany 95: 707-735, Oxford University Press on behalf of the Annals of Botany Company, United States (2005).
European Search Report from European Patent Application No. 06757522.5, European Patent Office, Munich, Germany, dated Apr. 22, 2009.
English Language Translation (1 page) of Antoni, H.J. and Folquerm F., "In Vitro Tisse Culture of *Ipomoea batatas* (L.) Lam. Sweet Potato for the Production of New Cultivars," *Revisita Agronomica del Noroeste Argentino* 12:177-8, Universidad Nacional de Tucuman, Facultad de Agronomica y Zootecnia, Argentina (1975).
Restriction/Election Requirements in U.S. Appl. No. 12/889,026, inventors Jin, Y.W., et al., filed on Sep. 23, 2010, mailed on Sep. 19, 2011, U.S. Patent and Trademark Office, Alexandria, VA.
Office Action in U.S. Appl. No. 12/889,026, inventors Jin, Y.W., et al., filed Sep. 23, 2010, mailed in Dec. 21, 2011, U.S. Patent and Trademark Office, Alexandria, VA.
English language Abstract of Korean Patent Publication No. KR 10-2005-0102571 A, European Patent office, espacenet database—Worldwide, (2005).
English language Abstract of Korean Patent Publication No. KR 10-2005-0041259 A, European Patent Office, espacenet database—Worldwide, (2005).
English language Abstract of Korean Patent Publication No. KR 10-2004-0014584 A, European Patent Office, espacenet database—Worldwide, (2004).
English language Abstract of Korean Patent Publication No. KR 10-2005-0078372 A, European Patent Office, espacenet database—Worldwide, (2005).
English language Abstract of Korean Patent Publication No. KR 10-2000-0056501 A, European Patent Office, espacenet database—Worldwide, (2000).

* cited by examiner

ISOLATED POPULATION OF PLANT SINGLE CELLS AND METHOD OF PREPARING SAME

CROSS-REFERENCE TO RELATED APPLICATIONS

This application is a continuation application of U.S. application Ser. No. 12/117,783, filed on May 9, 2008, now U.S. Pat. No. 8,053,238, which is a continuation-in-part application of U.S. application Ser. No. 12/063,929, 371(c) date of Feb. 15, 2008, now U.S. Pat. No. 8,017,397, which is a U.S. national phase of International Application No. PCT/KR2006/001544, filed on Apr. 25, 2006, which claims the benefit of Korean Application No. 10-2005-0103445, filed on Oct. 31, 2005, the contents of which are hereby incorporated by reference in their entireties.

TECHNICAL FIELD

Plant has been used very importantly not only as our food supply but also as the source of extensive chemical substances including, pharmaceuticals, fragrances, colors, agricultural chemicals and dyes etc. Biologically active compounds that are produced from plants are mostly secondary metabolites. There is a greater interest on the secondary metabolites, such as alkaloid, allergen, amino acid, anthraquinone, antileukaemic agent, antimicrobial agent, antitumor agent, antiviral agent, enzyme, flavonoids, insecticide, opiate, perfume, pigment, vitamin, and polysaccharide etc., because most of them work as physiologically active substances. According to Zhong (2002), there are about 100,000 known plant secondary metabolites and more than 25% of the medicine that are practically used is plant-derived substances. Every year, novel secondary metabolites are discovered continually.

In the method of obtaining these metabolites, there are many problems such as difficult chemical synthesis in spite of the recent astonishing developments of the organic chemistry, demolition of the nature due to exploitation and environmental pollution and changes of the content of metabolites and increase of the production cost depending on the culture conditions, e.g., season, region and climate. Therefore, there are on going active attempts to produce secondary metabolites through in vitro culture technique which has advantages of controlling the adequate external environmental conditions and producing on a large scale even in a small space.

BACKGROUND ART

According to Korean Patent No. 0130100, production of biologically active substances through plant cell culture has more advantages than direct extraction from the plant. Plant cell culture is considered as an optimal method for continual production which is not influenced by environment and for solving the pending problems like destruction of ecology.

Nail & Roberts (2004), however, indicated slow growth rate and low productivity of the plant cell culture for the secondary metabolite production. To solve this problem, there have been studies of the optimization of the media, culture conditions, process and elicitation for higher productivity etc. (Zhong 2002). As disclosed in WO93/17121, various media was used to culture diverse *Taxus* for the increase in cell growth rate and paclitaxel productivity. Based on the results of the experiments, elicitation conditions for paclitaxel mass production was indicated. Despite the improvements to the production of valuable secondary metabolites, variability is still a major issue for the production of paclitaxel from *Taxus* and other valuable substances from numerous plant systems.

Production of secondary metabolites through large scale plant cell culture is commercially possible only when there is a stable maintenance of rapid cell growth and high metabolite production during long term culture. The ability of the cell lines that could produce distinct metabolites are not stable which cause the cell lines to lose their initial productivity through subcultures; it is not too much to say that success and failure are depended on how we overcome these problems.

In plant cell culture, although the cells are derived from one plant, metabolite productivity of each cell line is different and unstable. Therefore, establishing the cell lines that have high productivity and genetic stability is most important than anything else.

Cell Lines Derived from Single Cells & and Multiple Cells

Plant cell lines derived from single cells have lower variability than the cell lines derived from multiple cells; this results in higher productivity. In preceding inventions, stem, root, seed, needle and leaf were used as the best explants for cell line induction. These stem, root, seed, needle and leaf are tissues that are composed of the cells with distinct functions and morphology. Callus, cell lines derived from these tissues is not of one kind. Therefore, there are limitations on the attempts to reduce the productivity variation of the callus derived from the tissues consisted of multiple cells.

Cell Aggregation

One of the distinguishing characteristics of plant cell culture is cell aggregation. According to Korean Patent No. 0364478, diameter of the plant cell is 30-300 μm which is about 30 times bigger than the animal cell. Because plant cell walls have natural tendency to adhere together, it is not possible to obtain suspension which consists only of dispersed single cells. The proportion and the size of cell aggregates vary according to plant variety and the medium in which the culture is grown. Nail & Roberts indicated that cell aggregation leads to a difference in local environment between interior and exterior of the cells, which can result in culture heterogeneity and ultimately leads to changes in growth and metabolism.

The purpose of suspension culture is to obtain pure single cells. To accomplish this objective, filtration, maceration and protoplast culture by using enzyme were used. However, filtration and maceration do not provide complete pure single cells. Protoplast culture technique which eliminates the cell wall is the most reliable method for generating single cells, but the enzyme used for the protoplast culture cause cell wall damages or breakages that result in the change of cell physiology. Moreover, hydrophobic secondary metabolites such as paclitaxel can be stored in the cell wall, so the changes in the cell wall have profound relationship with productivity.

Also, cell aggregation has long been a major obstacle to the accurate measurement of cell growth by number and to biochemical assays to individual cells. According to Nail & Roberts (2004), if single cell culture is possible, it will readily provide faster information about the behavior of cell units in the culture such as biosynthesis, storage, and degradation etc. of secondary metabolites.

Dedifferentiation

The dedifferentiated cell line, which is callus, shows great variability in the production of secondary metabolites due to somaclonal variation. Callus derived from the permanent tissues such as leaves, stem, root and seed that are composed of the cells with distinct functions and morphology usually show dramatical changes even on slightly different microenvironments because it is a secondary meristem formed by dedifferentiation. Due to this sensitivity, Hirasuna et al. (1996) investigated to identify the cell culture conditions, especially initial cell density, subculture interval and temperature, and to maintain them as precisely as possible.

Scale Up

In order to produce secondary metabolites through plant cell culture for commercialization, scale up is essential. Bioreactor has been applied for mass production after many patents and articles were published, reporting about successful production of metabolites through cell culture in a laboratory scale. According to Korean Patent No. 0290004, application of bioreactor for mass production provides very different culture environment from the flask in a laboratory scale which results in the decrease in growth rate and productivity and change in the metabolites. When the bioreactor is applied for mass production, changes in growth rate, productivity and metabolites have become problems in commercialization of biologically active substances through cell culture. In the scale up of plant cell cultures, a bioreactor which receives the air through exterior power and/or a bioreactor with impeller by considering the efficiency of the mixing and aeration are preferred. However, cell viability decreases abruptly in the bioreactor because plant cells are weak for shear. Therefore, a method to reduce shear is necessary. The cause of the shear sensitivity of the plant cell is explained by its large size, rigid cell wall, aggregation and extensive vacuolate (Yokoi, et al., 1993). To solve these problems associated with the bioreactor, a low shear generating bioreactor was investigated in the past by controlling its agitating speed and modifying the impeller type. However, it still bears negative results because the cell lines could not overcome the differences of the microenvironment.

Cryopreservation

Cryopreservation allows the long term cell maintenance by ceasing most of the metabolism of the cells in the extremely low temperature. It signifies the recovery of the cells without genetic, characteristics and biosynthetic variation after cryopreservation. By using cryopreservation, loss of the cells from contaminations could be eliminated and the genetic variation in the continuous cell lines could be minimized. In cGMP, the preservation of the cell lines for a long period is mandatory for the stable supply of raw materials. Usually, cultured animal cells could undergo cryopreservation for many years, but the similar cryopreservation technique is much more challenging for cultured plant cells. Cultured plant cells are heterogeneous and show diversity in physiology and morphology. Therefore, plant suspension cells require many processes for cryopreservation and inadequate cryopreservation could cause variability.

Conditioning Factors

Kim et al. (2000) demonstrated that cell division can be stimulated if some media from actively dividing cultures was added to the cultures that lost cell division ability. In the production of anthocyanin through rose suspension culture, the productivity increased when some media of strawberry suspension culture was added to the rose suspension culture. In this way, the substances that were produced and secreted from the cultured cells to stimulate the cell growth or the production of the secondary metabolites are called conditioning factors. Yet, these conditioning factors have not been identified concretely and there are only some understanding of conditioning factors acting as chemical signals for the cell growth and metabolite production. Also, there are few reports on the potent substances, such as phosphates and calmodium which could be considered as conditioning factors. Conditioning factors can be supplied through conditioned media or helper cells.

Perfusion Cultivation

Among the cell culture methods, there is a batch cultivation involving the inoculation of the cell and the media together in the beginning and no further nutrition supplementation. Also, there is a continuous cultivation, involving the supplementation of the new media as the spent media that contains metabolites is retrieved simultaneously at a consistent speed during the culture period for the prevention of nutrition depletion.

Batch cultivation is difficult in the commercial level due to its low productivity. Among the continuous culture methods, perfusion cultivation is receiving much attention these days. In perfusion culture, the cells are remained in the bioreactor, and new media is supplied as the spent media that contains metabolites is retrieved.

According to Zhang et al. (2000), elicitation is one of the most effective ways to promote the secondary metabolites production in cell culture. Elicitation encourages secondary metabolite synthesis, but it induces cell growth inhibition and the rapid decrease in the cell viability. Hence, secondary metabolite synthesis by elicitation could be maintained only for a short period and it is very limited. As Wang et al. (2001) presented, perfusion cultivation is a strategy to minimize these negative effects by elicitation and to maximize the productivity.

Wang et al. (2001) and Wu & Lin (2003) reported as follows. Secondary metabolites that are produced by elicitation are stored inside the cell (vacuole or cell wall) or released outside the cell (media). During the process of culture, releasing secondary metabolites from the cell and removing it from the media could bring easier purification and could diminish the feedback inhibition of biosynthesis and degradation and conversion of the products. Therefore, by retrieving the spent media and supplying with a new media, secretion of internal and external metabolites could extend the viability and biosynthesis of the cells, which could remarkably increase the productivity.

Storage and the secretion of secondary metabolites showed great differences depending on the cell lines. *Taxus* media cell line (Wickremesinhe and Arteca 1994) did not excrete any. Consequently, establishing cell lines that have outstanding secretion ability is required.

Cambium Culture

Cambium is a lateral meristem that is located on the lateral side of the plant. In the gymnosperm and woody dicotyledon plants, there is a hypertrophic growth due to the continual activity of the cambium; as a result, giant plants having more than 11,000 years of the growth rings exist. In genetics, meristems could be classified as primary and secondary meristem. Primary meristem represents the meristem that forms during embryogenesis and participates in the plant growth after seed germination. Secondary meristem represents the meristem that is formed by dedifferentiation of the plant permanent tissue. Cambium is a primary meristem with meristematic continuity derived from procambium without the intervene of the permanent tissue.

Growth of this primary meristem is indeterminate and could be continued if the conditions are given. Therefore, cambium culture has been used for rapid mass propagation of the cells.

In the preceding studies, cambium explants were prepared as follows: after the bark was peeled off, two longitudinal cuts, approximately 1 mm deep in order to reach the xylem, were made into the woody stem at an interval of 5 mm. The resulting explants were called 'cambium', which was constituted of part of the phloem, cambium and a small chip of xylem (Jouira et al., 1998).

It is reasonable to say that cells which are induced by the method as mentioned above are not the sole origin of cambium, but of multiple tissues, which can be solemnly distinguished anatomically such as phloem, cambium and xylem. Thus, we could indicate that the method mentioned above is not the ideal technique to separate only the cambium elaborately from the various tissues that constitute the stems. A creative method to separate only cambium or procambium from the various tissues of stems has been in demand.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention is provide to resolve the problems associated with the prior art, e.g., variation occurred in plant cell culture.

One objective of the present invention is to provide a method of producing a single cell clone or a population of single cells by isolating and culturing only cambium or procambium from a plant.

Another objective is to provide a method of stably producing biologically active substance (e.g., paclitaxel) or substances from the single cell clone or the population of single cells.

To achieve the above objectives, in one aspect, the present invention provides a method for isolating a plant cambium-derived or procambium-derived single cell clone, the method comprising: (a) preparing and then sterilizing a plant tissue; (b) collecting the tissue containing cambium or procambium from the sterilized plant tissue; (c) culturing the tissue containing cambium or procambium, and thereby inducing a cambium or procambium layer which is proliferated from cambium or procambium, and a callus layer which is derived from regions except cambium or procambium and proliferated in an irregular form; and (d) isolating the single cell clone from the cambium or procambium layer.

Preferably, the step (c) comprises culturing the said tissue in medium containing auxin. In a preferred embodiment, the medium contains 1~3 mg/L of auxin.

In another aspect, the present invention provides a single cell clone induced from plant cambium or procambium, the single cell clone comprises the following characteristics: (a) above 90% cells in suspension culture exist as single cells; (b) having multiple vacuoles morphologically; (c) growing faster than the cell line derived from regions except cambium or procambium of the same plant origin, and culturing stably for a long time; (d) having low sensitivity to shear stress in the bioreactor; and (e) being innately undifferentiated.

Preferably, the plant is the genus *Taxus*. In a preferred embodiment, the genus *Taxus* cambium-derived or procambium-derived single cell clone has an ability of releasing paclitaxel 270-720 or 404-1077 times more than the cell lines derived from regions except cambium or procambium of the same plant origin.

In still another aspect, the present invention provides a method for producing plant-derived biologically active substances, the method comprising the steps of: (a) producing the active substances by culturing the above single cell clone; and (b) collecting the active substances. Preferably, the culturing in the step (a) comprises retrieving the media used in culturing of the single cell clone culture and then supplying with a new media.

In a preferred embodiment, the single cell clone is the genus *Taxus* cambium-derived or procambium-derived single cell clone, and the compound is paclitaxel. In this case, the media may further contain one or more materials selected from the group consisting of methyl jasmonate, phenylalanine and chitosan.

In a further aspect, the present invention provides a method for preserving a plant cell line. The method comprises cryoperservating single cells derived from plant cambium or procambium, which are isolated by the above-described method.

In accordance with the present invention, it is possible to culture single cell clone that has the meristematic continuity of primary meristem without going through dedifferentiation by precisely separating only cambium or procambium from various tissues of woody plant twig or stem. Cell line of the present invention allows stable production of biologically active substances due to less change in the cell growth rate and growth pattern during the long term culture. It is also optimal for the mass production in commercial level because it is less sensitive to shear in a bioreactor compared to the cell lines derived by the preceding techniques, due to less aggregation and multiple vacuoles.

Metabolite activation can be stimulated by supplementing conditioning factors to this cell line and cell vitality and biosynthesis can be extended as the cells releasing considerable amount of production into the extracellular media through perfusion culture. High recovering rate after cryopreservation due to homogeneity and division ability of this cell line devises the establishment of cell bank. Through the present invention, close relationship between homogeneity of the cultures and variation of secondary metabolites are confirmed, and the strategy for commercialization may be developed as the variability of diverse biologically active substance production can be controlled and reduced.

The above and other features and advantages of the present invention will be apparent from or are set forth in more detail in the accompanying drawings, which are incorporated in and form a part of this specification, and the following Detailed Description, which together serve to explain by way of example the principles of the present invention.

BRIEF DESCRIPTION OF DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

DETAILED DESCRIPTION OF THE DISCLOSURE

Practical examples of the invention are explained below. Induction and proliferation method of single cell clone from cambium or procambium is not only utilized in paclitaxel production system but it may also be utilized in all plant secondary metabolite production system. The following examples are offered by way of illustration, not by way of limitation.

Practical Example 1

Preparation of Plant Materials and Isolation of Cambrium or Procambium

Seed, needle, twig of the yew tree were collected. After collecting the materials, they were deposited in the solution of 100 mg/L of antioxidant, ascorbic acid (L-ascorbic acid, DUCHEFA, The Netherlands) immediately and transferred and preserved. They were surface sterilized by considering the morphology and physiological characteristics of the materials.

1. Seed: After sterilizing the seeds with 70% ethanol for one minute, they were immersed in 1% Clorox solution for 48 hours and were washed 3 to 4 times with sterile water. Next, embryo was separated from the seed in the solution of 0.5% PVP (polyvinyl pyrrolidone, DUCHEFA, The Netherlands) and 50 mg/L of ascorbic acid (L-ascorbic acid, DUCHEFA, The Netherlands), and 70 mg/L of citric acid (DUCHEFA, The Netherlands) and cultured on the callus induction media.

2. Needle and twig: After 24 hours of treatment with the solution containing 1% Benomyl (Dongbu Hannong Chemical, Korea)+1% Daconil (Dongbu Hannong Chemical, Korea)+1% Streptomycin sulphate (DUCHEFA, The Netherlands)+0.1% Cefotaxime sodium (DUCHEFA, The Netherlands), needles and twigs were rinsed with tap water for 30 seconds to remove the remaining chemical substances and phenolic compounds. After sterilizing them with 70% ethanol (DC Chemical, Korea) for one minute, 30% hydrogen peroxide (LG Chemical, Korea) for 15 minutes, 1% CLOROX solution for 15 minutes, 3% CLOROX solution for 5 minutes in order, they were washed 3 to 4 times with distilled water. To prevent the oxidation, both ends of the needle were cut in the solution of 5% PVP, 50 mg/L ascorbic acid and 70 mg/L citric acid and cultured on the callus induction media.

3. Cambium or procambium preparation from the twig or stem: By holding the xylem which is the center region of the twig or stem with the tweezers, phloem and cortex and epidermis tissues including cambium or procambium were peeled off. These peeled tissues that contained cambium or procambium were laid on the media; cambium or procambium was allowed to touch the surface of the media.

Practical Example 2

Induction of Single Cell Clone from the Isolated Cambium or Procambium

Figure 1:
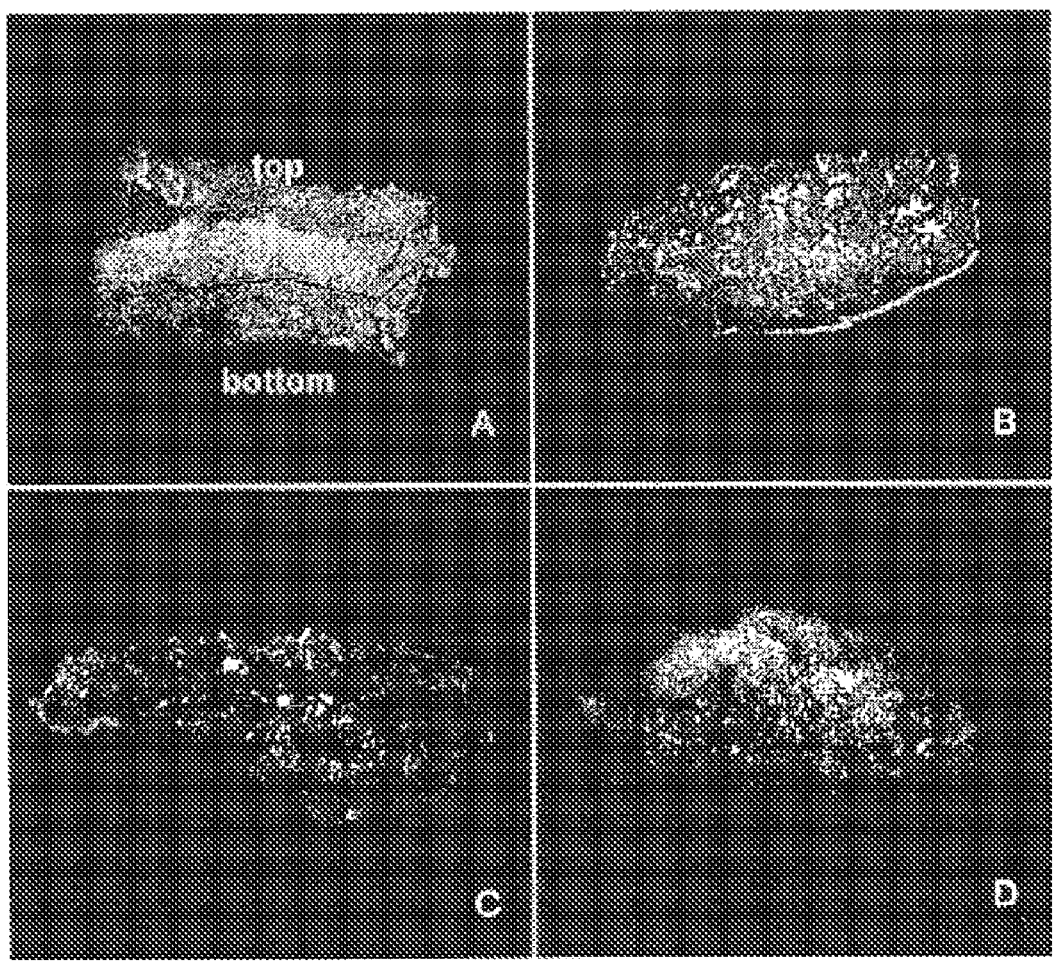
FIG. 1A shows a twig after 30 days of cultivation in which procambium (bottom) is separated from callus cells derived from tissue which consists of phloem, cortex, and epidermis.
FIG. 1B shows a single cell clone derived from procambium after 35 days of cultivation.
FIG. 1C shows callus derived from tissue which consists of phloem, cortex, and epidermis after 40 days of cultivation.
FIG. 1D shows callus derived from embryo or needle after 50 days of cultivation.

After 4th to 7th day of the culture, cell division of cambium or procambium was observed and on the 15th day of the culture, callus was beginning to form from the layer consisted of the phloem and cortex and epidermis that were the upper part of the cambium or procambium. On the 30th day of the culture, the cambium or procambium began to be separated from the upper layer tissue that contained the phloem and cortex and epidermis; after these two layers were completely separated naturally, they were cultured individually on different petri dishes (FIG. 1).

For the purpose of cell and callus induction, universally known media of the plant cell and tissue culture could be used: e.g. mB5 (modified Gamberg's B5 medium), MS (Murashige & Skoog medium), WPM (Lloyed & McCown), SM (schenk & Hildebrand medium), LP (Quoirin & Lepiovre). Application of all these media is possible. Various additives could be supplemented and components of the media could be reduced or eliminated as the need arises. Among them, the most appropriate media was mB5. The contents of mB5 are described in the following Table 1.

TABLE 1

CELL LINE INDUCTION & MAINTENANCE MEDIUM IN *TAXUS* SPP.

| | Composition | Contents (mg/L) |
|---|---|---|
| Inorganic salts | $KNO_3$ | 2500 |
| | $(NH_4)_2SO_4$ | 134 |
| | $MgSO_4 \cdot 7H_2O$ | 121.56 |
| | $MnSO_4 \cdot 4H_2O$ | 10 |
| | $ZnSO_4 \cdot 7H_2O$ | 2 |
| | $CuSO_4 \cdot 5H_2O$ | 0.025 |
| | $CaCl_2 \cdot 2H_2O$ | 113.23 |
| | KI | 0.75 |
| | $CoCl_2 \cdot 6H_2O$ | 0.025 |
| | $NaH_2PO_4 \cdot H_2O$ | 130.44 |
| | $H_3BO_3$ | 3 |
| | $Na_2MoO_4 \cdot 2H_2O$ | 0.25 |
| | FeNaEDTA | 36.7 |
| Vitamin | Myo-inositol | 200 |
| | Thiamine-HCl | 20 |
| | Nicotinic acid | 2 |
| | Pyridoxine-HCl | 2 |
| | L-ascorbic acid | 50 |
| | Citric acid | 75 |
| Amino acid | L-aspartic acid | 133 |
| | L-arginine | 175 |
| | Glycine | 75 |
| | Proline | 115 |
| Hormone | a-Naphtalene acetic acid | 2 |
| Sucrose | | 10,000 |
| Activated charcoal | | 100 |
| Gelrite | | 2,000 |

The cultures were grown on the media that was supplemented with a plant growth regulator, auxin (1-3 mg/L) in the dark at 25±1° C.

The cambium or procambium was composed of homogeneous cells, so its cell division was uniform and proliferation occurred in the form of a plate. On the other hand, the tissue containing the phloem and cortex and epidermis proliferated in irregular form because there was a discrepancy of cell division due to the composition of many kinds of cells. There was a self-split of the layer in between the cambrium or procambium and the tissue containing phloem and cortex and epidermis (FIG. 1). The cambrium or procambium was homogeneous and the tissue containing phloem and cortex and epidermis was heterogeneous, so the self-split of the layer seemed to be the result of different division rate.

After 15th day of the culture, calli were formed on the explants of embryo and needle that are composed of heterogeneous cells by differentiation and these calli proliferated in irregular forms due to the different division rate of various cells just like the tissue that contained phloem and cortex and epidermis. (FIG. 1)

Practical Example 3

Establishment of Long Term Culture

Among the calli, white and friable calli that had good growth rate were subcultured onto the new media every 14 days. The growth rate of the embryo and needle-derived cultures was very unstable and it often showed the tendency of browning. On the contrary, the growth rate of the cambrium-derived or procambium-derived cultures was fast and there was no color change of the cultures. Therefore, it was possible to select the stable cells.

After six months of the culture, most of the embryo and needle-derived cultures had yellow or light brown color and aggregation formed. The procambium-derived or cambium-derived cultures had white-yellow color and were maintained as single cells or small cell clusters. The growth rate of the cultures that turned brown and formed aggregation slowed down and the cultures died eventually because of the phenol chemical substance that they excreted.

Figure 2:
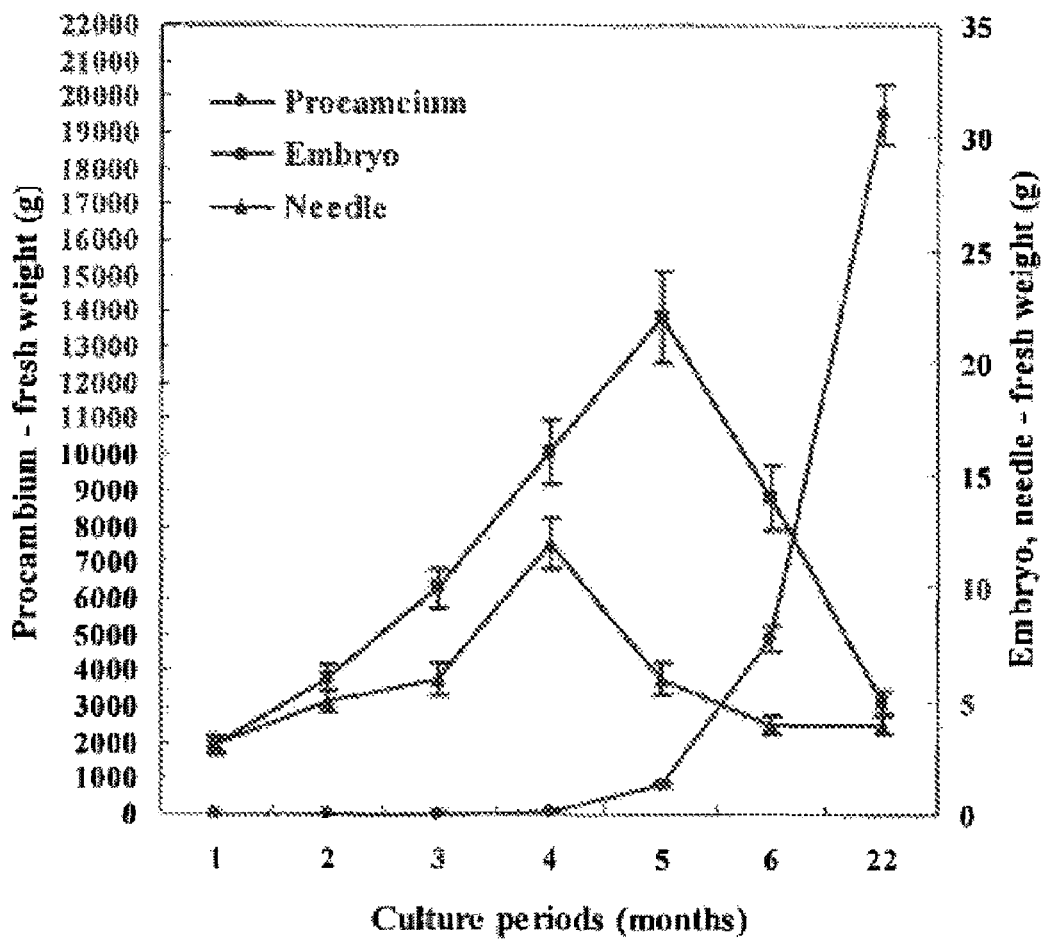
FIG. 2 show growth rate expressed by total biomass production of three different *T. cuspidata* cell cultures derived from procambium, embryo, and needle in 22 months with the subculture interval ranged between 14 days.
Figure 3:
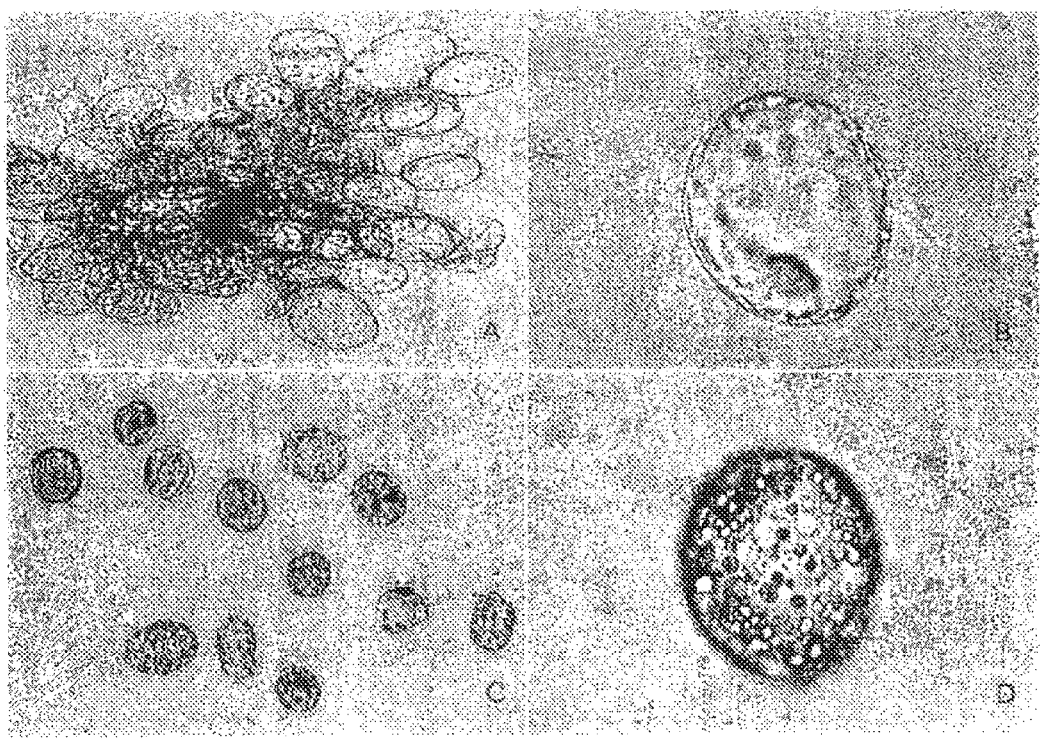
FIG. 3 A-D show images of cell aggregation of two different *T. cuspidata* cultures derived from embryo or needle (A, C) and procambium (B, D), in which A shows large cell aggregates with the size of 1.5×10² μm, B shows single cell population, D shows cells presenting a high density of vacuole.

According to this inventor, maintenance and mass proliferation of the embryo and needle-derived cultures was difficult after 6 months, but the cambium-derived or procambium-derived cultures were maintained stably for more than 20 months of the long term culture without any variation in the rate of cell growth, growth pattern and aggregation level (FIG. 2). In other words, variability appeared in growth pattern, depending on the homogeneity and heterogeneity of the initial plant materials.

Practical Example 4

Establishment of Cell Suspension Culture

The embryo and needle-derived and the cambium-derived or procambium-derived cultures were cultured individually in the flask containing the liquid media (Table 2).

TABLE 2

SUSPENSION MEDIUM IN *TAXUS* SPP.

| | Composition | Contents (mg/L) |
|---|---|---|
| Inorganic salts | $Ca(NO_3)_2$ | 471.26 |
| | $NH_4NO_3$ | 400 |
| | $MgSO_4 \cdot 7H_2O$ | 180.54 |
| | $MnSO_4 \cdot 4H_2O$ | 22.3 |
| | $ZnSO_4 \cdot 7H_2O$ | 8.6 |
| | $CuSO_4 \cdot 5H_2O$ | 0.25 |
| | $CaCl_2 \cdot 2H_2O$ | 72.5 |
| | $K_2SO_4$ | 990 |
| | $Na_2MoO_4 \cdot 2H_2O$ | 0.25 |
| | $H_3BO_3$ | 6.2 |
| | $KH_2PO_4$ | 170 |
| | FeNaEDTA | 36.7 |

TABLE 2-continued

SUSPENSION MEDIUM IN *TAXUS* SPP.

| | Composition | Contents (mg/L) |
|---|---|---|
| Vitamin | Myo-inositol | 200 |
| | Thiamine-HCl | 20 |
| | Nicotinic acid | 2 |
| | Pyridoxine-HCl | 2 |
| | L-ascorbic acid | 50 |
| | Citric acid | 75 |
| Amino acid | L-aspartic acid | 133 |
| | L-arginine | 175 |
| | Glycine | 75 |
| | Proline | 115 |
| Hormone | a-Naphtalene acetic acid | 2 |
| Sucrose | | 30,000 |

They were cultured on the 100 rpm rotating shaker in the dark at 25±1° C. With the two weeks of subculture interval, cultures were allowed to maintain high vitality continuously as exponential growth phase.

Aggregation level which is the main cause of the variation of cell productivity was measured. Cell aggregate quantification was measured with the biological microscope (CX31, Olympus, Japan). The result of the experiment described above is on Table 3.

TABLE 3

TYPE OF CELL AGGREGATES OF *TAXUS* LONG-TERM CULTURES

| Large cell aggregates | Moderate cell aggregates | Small cell aggregates | Single cell population | Explant source |
|---|---|---|---|---|
| 60 ± 3.2% | 30 ± 3.3% | 7 ± 0.6% | 3 ± 0.9% | embryo, needle |
| 0 | 0 | 7.4 ± 0.8% | 92.6 ± 0.8% | procambium |
| 0 | 0 | 9% | 91% | cambium |

Large cell aggregates, size higher than $1.5 \times 10^3$ μm;
Moderate cell aggregates, $1 \times 10^3$ μm;
Small cell aggregates, $4 \times 10^2$ μm < size < $1 \times\times 10^3$ μm in case of the suspension of the embryo and needle-derived cultures, about 60% had cell aggregation size more than 1.5 mm but in the suspension of the procambium-derived cultures or cambium-derived cultures, 92.6% or 90% of the cells, respectively, were cultured as single cells.

Practical Example 5

Scale Up

The embryo and needle-derived and the cambium-derived or procambium-derived cultures were cultured in 3L airlift bioreactor (Sang-Won SciTech, Korea) in the dark at 25±1° C.

In case of the embryo and needle-derived cultures, there was a great variability in the size and shape of the cells compared to the flask culture, Diameter of the cell aggregation was enlarged up to 2-3 mm, which inhibited the flow inside of the bioreactor and developed unmixed region in the bioreactor. Growth ring formed by the cells adhering to the internal wall of the bioreactor. Cells in the center of the growth ring died after 20 days because the media was not supplied efficiently. Eventually dead cells excreted toxic substances and these substances lowered the vitality of all cells in the bioreactor. On the opposite, less aggregation of the cambium-derived or procambium-derived cultures caused smooth air circulation in the bioreactor; hence it was possible to diminish the amount of air supply from 200 ml to 150 ml per minute and the amount of developed bubble on the surface of the media was greatly reduced.

Doubling time of the embryo and needle-derived cultures in the flask was 12 days but it was lengthened to 21 days in the bioreactor. It was because of the growth ring formation and rapid decrease of cell viability due to sensitiveness to shear by cell aggregation and rigid cell wall. Doubling time of the cambium-derived or procambium-derived cultures was 4 to 5 days and there was no difference in the flask and the bioreactor, rather it was shortened in the bioreactor (Table 4). The procambium-derived or cambium-derived cultures formed very small growth ring in the bioreactor and the growth ring was dissolved easily by agitating the media with a simple stimulus. Moreover, there was no decrease in cell viability due to less sensitivity to shear by less cell aggregation and multiple vacuoles.

RELATIONSHIP BETWEEN DOUBLING TIME PATTERNS AND EXPLANT SOURCE IN *T. CUSPIDATA* CELL CULTURES IN FLASK AND BIOREACTOR

| Explant source | Doubling time(day) | |
|---|---|---|
| | flask | bioreactor |
| Embryo | 11.5 ± 1.3 | 21 ± 2.6 |
| Needle | 12 ± 2 | 21 ± 2 |
| Procambium | 5 ± 0.2 | 4 ± 0.1 |
| Cambium | 5 | 4 |

Practical Example 6

Elicitor

Figure 4:
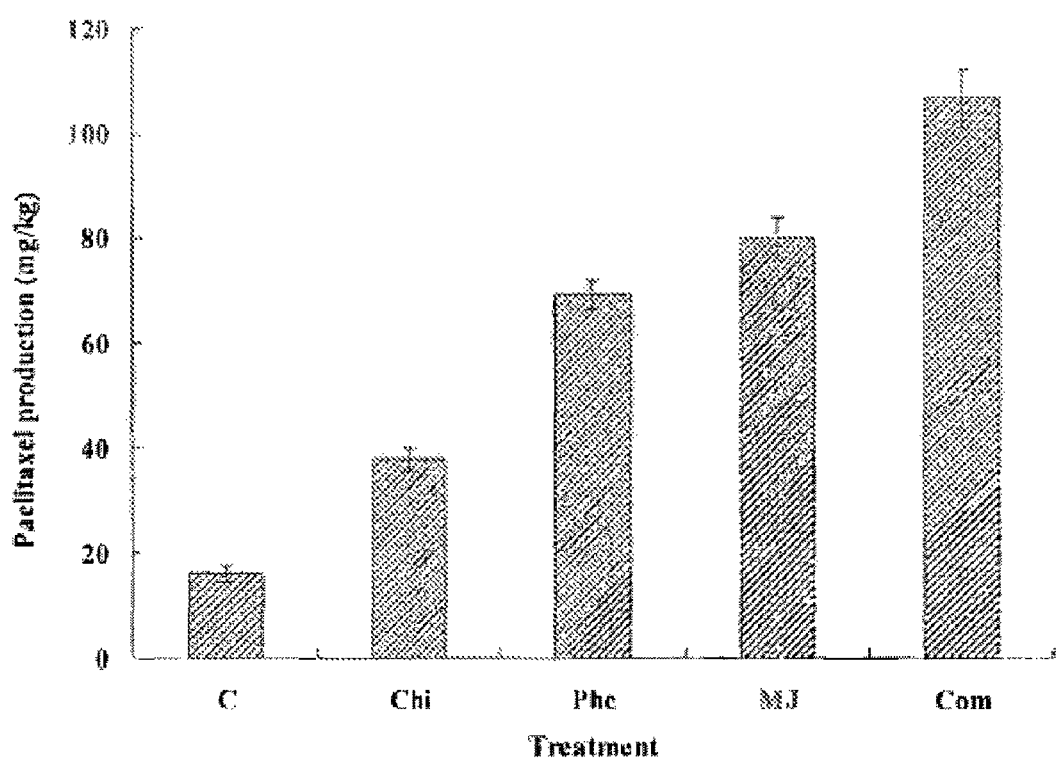
FIG. 4 is a graph showing the effect of elicitors and their combinations on paclitaxel production in *T. cuspidata* (single cell clone from procambium) cultures, in which conditioning factors were incorporated to zero-day cultures; C, control; Chi, 50 mg/L Chitosan; Phe, 0.1 mM Pheylanine; MJ, 100 μM Methyl Jasmonate; Com, combination of 50 mg/L Chitosan, 0.1 mM Pheylanine, and 100 μM Methyl Jasmonate.

Elicitor controls molecular signal in plant cells and is widely used for the increase of secondary metabolite productivity. After the treatment of methyl jasmonate as an elicitor and 10 other kinds of elicitors, we observed that methyl jasmonate had positive effect on the paclitaxel production. It was possible to obtain relatively high metabolites productivity through the combination of methyl jasmonate and other elicitors. Especially, paclitaxel production was very effective with the treatments of methyl jasmonate, chitosan and phenylanine (FIG. 4).

Practical Example 7

Conditioning Factors

Plant derived secondary metabolites are produced when the cells are growing or when the cells stopped growing. Therefore, two stage cultures are suitable for the production of metabolites like paclitaxel whose cell growth stage and metabolite production stage are separated. In the first stage, cells were proliferated in a large scale by optimizing the cell growth and in the second stage, the culture condition was changed for the optimization of metabolites production.

Cell lines with high secondary metabolites productivity grow slower and die faster than the cell lines with low productivity. Therefore, mass proliferation is difficult a d mass production of the metabolites is impossible.

Figure 5:
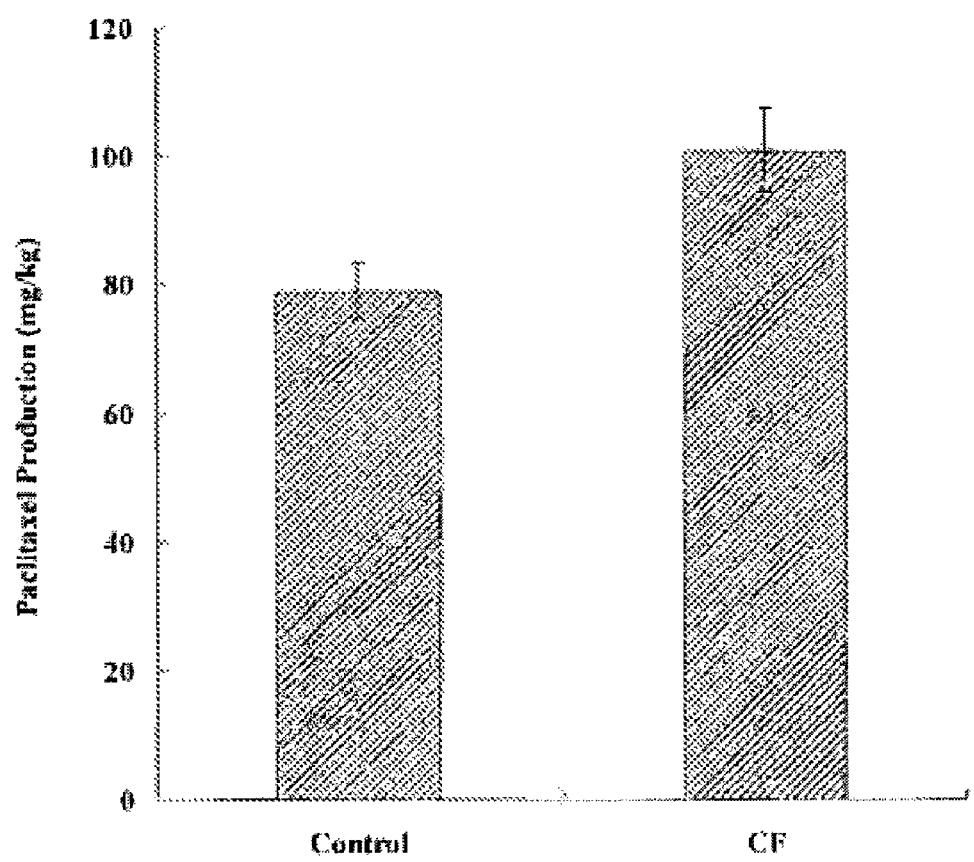
FIG. 5 is a graph showing the effect of conditioning factors on paclitaxel production in *T. cuspidata* (single cell clone from procambium) suspension culture, in which elicitors were incorporated to 14-day old cultures; CF, conditioning factors.

In this invention, cell lines with the ability of low proliferation and high production were not used for the proliferation in large scale, rather they were used as the helper cells that have the conditioning factors for the production of secondary metabolites. We observed the paclitaxel production after adding the helper cells. The results are summarized in FIG. 5.

Practical Example 8

Perfusion Culture

On the 14th day of culture, elicitor was treated to the embryo and needle-derived and the cambium-derived or procambium-derived cultures. From the point of elicitation, spent media was retrieved in an aseptic condition with pipette on every 5 days and was supplied with the same amount of new media simultaneously. The production of paclitaxel in the cell and the media were observed after 45 days of the long term culture. The result was summarized in Table 5.

TABLE 5

PACLITAXEL PRODUCTION AND RELEASE OF *T. CUSPIDATA* CELLS IN VARIOUS EXPLANT SOURCES AND PROCESSES

| Materials & processes | Taxol yield (mg/kg) | | | |
|---|---|---|---|---|
| | In cell | In medium | Total(days) | Taxol release(%) |
| embryo | 12.97 ± 1.16 | 0.03 ± 0.01 | 13 ± 1.17 (28) | 0.2 ± 0.1 |
| Needle | 10.92 ± 1.6 | 0.08 ± 0.01 | 11 ± 1.6 (28) | 0.7 ± 0.1 |
| Procambium | 86.4 ± 6.7 | 32.3 ± 7.6 | 118.7 ± 3.3 (28) | 27.1 ± 6.1 |
| Procambium | 0 | 0 | 0 (45) | — |
| Procambium perfusion culture | 65.5 ± 4.1 | 171.8 ± 11.1 | 237.3 ± 7 (45) | 72.3 ± 2.5 |
| Cambium | 76.4 | 21.6 | 98 (28) | 22 |
| Cambium | 0 | 0 | 0 (45) | — |
| Cambium perfusion culture | 69 | 195 | 264 (45) | 74 |

Depending on the cell lines, paclitaxel release of the cell to the media was different. Paclitaxel releasing ability of the cambium-derived or procambium-derived cultures was superior to the cultures of the preceding techniques. The cambium-derived or procambium-derived single cell clone had an ability of releasing paclitaxel about 270-720 or 404-1077 times more than the cell lines derived from embryo and needle (in medium of Table 5). Moreover, application of perfusion culture facilitated the release of secondary metabolites to the media. Improvement in the extracellular release of secondary metabolites through the cambium-derived or procambium-derived single cell clone by exchanging the media periodically had great importance because it allowed continuous recycle of the biomass and simple purification.

In other words, periodical exchange of the media in the cambium-derived or procambium-derived single cell clone culture can be considered as a stable method of producing valuable metabolites in the long term culture, because it prevents feedback inhibition of accumulated metabolites in the cell, degradation and conversion of the metabolites in the media.

Practical Example 9

Cryopreservation

On the 6th or 7th day of the culture, suspension cells were pre-cultured in the media containing 0.16M of manitol for 3 days at the room temperature and then maintained at 4° C. for 3 hours. Cells were harvested and placed into 4 ml cryovial which had the media containing 40% ethylene glycol (Sigma, USA) and 30% sorbitol (DUCHEFA, The Netherlands) and cultured for 3 minutes at 4° C.

Suspension cells that were treated with cryopreservatives were frozen after the cells were soaked in the liquid nitrogen. For thawing, cultured cells in the liquid nitrogen for more than 10 minutes were thawed in the 40° C. water bath for 1-2 minutes. For the re-growth of the cells, cryopreserved cells were transferred onto the semi-solid growth media (Table 1) containing 0.5 M sorbitol and alleviated at the room temperature for 30 minutes. Cells were cultured on the semi-solid growth media containing 0.1M sorbitol for 24 hours. And then, the cells were cultured on the semi-solid growth media without sorbitol for 24 hours, twice. Cell viability was evaluated.

Practical Example 10

Analysis of Paclitaxel Content

After separating the cells from the media of the recovered samples, paclitaxel contents were analyzed. Cell mass was measured after drying the cells completely with vacuum desicator (Sam Shin Glass, Korea). About 100 mg (dry weight) of the cells were mixed with 4 ml solution (1:1 v/v) of methanol (Sigma, USA) and methylchloride (Sigma, USA) and were extracted by ultrasonic cleaner (Branson, USA) for 3 times in one hour interval at the room temperature. Cells were fully dried and extracted several times by using 4 ml of methylchloride. Separated organic solvent layer was vacuum dried and the remaining was dissolved in 1 ml of methanol. Dissolved extract was agitated equally by ultrasonic cleaner. Then, after centrifugation, the pellet was removed (8,000 g×5 min).

Media (1-5 ml) that was separated from the cell was combined with the same volume of methylchloride and was extracted 3 times after full agitations. After organic solvent was vacuumed and dried completely, it was dissolved in 0.5 ml of methanol again.

HPLC (High Performance Liquid Chromatography, Shiseido, Japan) was used for the analysis of the content and Sigma products were used for paclitaxel standard substances. Capcell pak (C18, MGII, 5 um, 3.0 mm.times.250 mm, Shiseido, Japan) was maintained to 40° C. by using the oven, and water and acetonitril (Burdick & Jackson, USA) (50:50, v/v) were combined for the mobile phase and dropped regularly with the speed of 0.5 ml/min. UV-VIS detector (227 nm, Shiseido, Japan) was used.

As described above, according to the present invention, single cell clone, a primary meristem which has the meristematic continuity without dedifferentiation, obtained by separating cambium or procambium purely from twig or stem resulted in higher productivity due to shorter doubling time and/or due to less change in the cell growth and growth pattern during the long term culture than the cell lines obtained by conventional techniques. In addition, the-thus obtained single cell clone facilitated scale up because of less aggregation and multiple vacuoles of the cell lines. The single cell clone also allowed recovery after cryopreservation without any genetic variation.

The invention claimed is:

1. A cell line from a plant comprising innately undifferentiated cells isolated from the plant meristem without going through dedifferentiation into callus.

2. The cell line of claim 1, wherein said innately undifferentiated cells are derived from cambium of the plant.

3. The cell line of claim 1, wherein said innately undifferentiated cells are derived from cambium of the stem of the plant.

4. The cell line of claim 1, wherein said cells comprise one or more characteristics selected from the group consisting of:
   (i) forming smaller-sized aggregates than the aggregates formed by cells derived from dedifferentiated callus of the plant;
   (ii) growing in a rate faster than cells derived from dedifferentiated callus of the plant;
   (iii) stably growing for a longer period than cells derived from dedifferentiated callus of the plant;
   (iv) having multiple vacuoles;
   (v) comprising a greater number of single cells than cells derived from dedifferentiated callus of the plant; and
   (vi) having lower sensitivity to shear stress in a bioreactor than cells derived from dedifferentiated callus of the plant.

5. The cell line of claim 4, which is homogeneous.

6. The cell lines of claim 4, wherein said growing of the cell in (ii) or (iii) is in a suspension culture.

7. The cell line of claim 4, wherein said plant is the genus *Taxus*.

8. The cell line of claim 7, wherein at least about 90% of said cells are single cells.

9. The cell line of claim 7, wherein said cells have one or more characteristics selected from the group consisting of:
   (i) the cells do not form aggregates larger than 1.5 mm;
   (ii) the cells do not form aggregates larger than 1.0 mm; and
   (iii) the cells can be stably grown in a culture for at least 20 months.

10. The cell line of claim 9, wherein said cells have a doubling time of about four days in a bioreactor or about five days in a flask.

11. The cell line of claim 1, wherein said cells produce one or more substances.

12. The cell line of claim 11, wherein said substances are secondary metabolites.

13. The cell line of claim 11, wherein said substances are produced in an amount higher than the substances produced in cells derived from dedifferentiated callus of the plant.

14. The cell line of claim 11, wherein said substances are produced more consistently than the substances produced in cells derived from dedifferentiated callus of the plant.

15. The cell line of claim 11, wherein said substance is selected from the group consisting of an alkaloid, an allergen, an amino acid, an anthraquinone, an antileukaemic agent, an antimicrobial agent, an antitumor agent, an antiviral agent, an enzyme, a flavonoid, an insecticide, an opiate, a perfume, a pigment, a vitamin, a polysaccharide, and combinations thereof.

16. The cell line of claim 11, wherein said plant is the genus *Taxus*, and wherein said substance is paclitaxel.

17. The cell line according to claim 16, wherein said cells produce paclitaxel 270-720 times more than cells derived from a dedifferentiated callus of said plant.

18. A method of isolating the cell line of claim 1 comprising:
(a) obtaining a tissue containing innately undifferentiated cells from a plant;
(b) culturing said tissue in medium, thereby inducing a layer proliferated from the innately undifferentiated cells; and
(c) collecting innately undifferentiated cells by isolating the layer.

19. The method of claim 18, wherein said layer proliferated from the innately undifferentiated cells in (b) is separated from a layer proliferated from dedifferentiated callus cells.

20. The method of claim 19, wherein said tissue of (a) is sterilized.

21. The method of claim 19, wherein said tissue in (a) is obtained by removing the tissue containing cambium or procambium from xylem tissue.

22. The method of claim 21, wherein said removing is by peeling off the tissue containing cambium or procambium from xylem tissue.

23. The method of claim 18, wherein said medium in (b) comprises auxin.

24. The method of claim 23, wherein said medium in (b) comprises 1-3 mg/L of the auxin.

25. A method for producing one or more biologically active substances, the method comprising the steps of: (a) culturing the cell line of claim 1 in a medium wherein said active substances are produced from the cell line, and (b) collecting said active substances.

26. The method of claim 25, wherein culturing in (a) comprises retrieving the medium used in culturing of said cells and then supplying with a new medium.

27. The method of claim 25, wherein said medium in (a) comprises one or more materials selected from the group consisting of methyl jasmonate, phenylalanine, and chitosan.

28. The method of claim 27, wherein said new medium comprises one or more materials selected from the group consisting of methyl jasmonate, phenylalanine, and chitosan.

29. A method of preserving a plant cell line, comprising cryopreserving the cell line of claim 1.

30. The cell line of claim 1, wherein said innately undifferentiated cells are derived from procambium of the plant.

31. The cell line of claim 1, wherein said innately undifferentiated cells are derived from procambium of the stem of the plant.

* * * * *